United States Patent
Mackey

(10) Patent No.: US 6,235,273 B1
(45) Date of Patent: May 22, 2001

(54) WASHABLE NON-TOXIC BODY PAINT FOR APPLYING COLOR TO HUMAN SKIN

(75) Inventor: Jack D. Mackey, Hawthorne, CA (US)

(73) Assignee: Mattel, Inc., El Segundo, CA (US)

( * ) Notice: Subject to any disclaimer, the term of this patent is extended or adjusted under 35 U.S.C. 154(b) by 0 days.

(21) Appl. No.: 09/497,455

(22) Filed: Feb. 3, 2000

(51) Int. Cl.$^7$ .......................... A61K 7/021; A61K 7/025; C09D 13/00
(52) U.S. Cl. .............. 424/63; 424/64; 424/401; 106/31.09; 106/31.1
(58) Field of Search ................. 424/401, 63, 64; 106/31.09, 31.1

(56) References Cited

U.S. PATENT DOCUMENTS

| | | |
|---|---|---|
| 3,409,574 | 11/1968 | Gros . |
| 3,993,492 | 11/1976 | Woolly . |
| 4,760,114 * | 7/1988 | Haaf et al. .............................. 525/66 |
| 4,978,390 | 12/1990 | Snedeker . |
| 5,084,098 | 1/1992 | Olson . |
| 5,275,806 | 1/1994 | Gbogi et al. . |
| 5,417,746 * | 5/1995 | Cheng ................. 106/19 B |
| 5,498,280 * | 3/1996 | Fistner et al. ....................... 106/19 B |
| 5,561,175 | 10/1996 | Imagawa . |
| 5,728,762 | 3/1998 | Reich et al. . |
| 5,735,940 | 4/1998 | Coller . |
| 5,744,126 | 4/1998 | Horino et al. . |
| 5,747,011 | 5/1998 | Ross et al. . |
| 5,753,244 | 5/1998 | Reynolds et al. . |
| 6,042,815 * | 3/2000 | Kellner et al. .......................... 424/63 |

FOREIGN PATENT DOCUMENTS

07216288 * 8/1995 (JP) .

* cited by examiner

Primary Examiner—Shelley A. Dodson
Assistant Examiner—Marina Lamm
(74) Attorney, Agent, or Firm—Roy A. Ekstrand

(57) ABSTRACT

A washable non-toxic body paint material is formed using two different weight polyethylene glycol waxes together with stearic acid, calcium carbonate, talc, titanium dioxide, guar gum, a preservative and a colorant. The material is formed by initially mixing dry granular form ingredients at room temperature. Once mixed, the material is subjected to a melt at approximately one hundred fifty degrees centigrade to form a paste which is poured within a mold to cool forming a dry cake. A moistened applicator activates the dry cake for use in body painting or other activities.

1 Claim, No Drawings

WASHABLE NON-TOXIC BODY PAINT FOR APPLYING COLOR TO HUMAN SKIN

FIELD OF THE INVENTION

This invention relates generally to play materials used by children and particularly to play materials utilized for applying color to skin areas.

BACKGROUND OF THE INVENTION

A variety of products have been provided through the years by practitioners in the toy arts and related arts which are variously applied to areas of a child user's skin in some fashion. For example, products have included play makeup, washable tattoos, face painting and body painting. All of the foregoing activities are relatively similar and may be generally described as "body painting". Thus, as used herein, the term "body paint" or "body painting" will be understood to be generally inclusive of the various types of activities and materials in which a colorant is applied to human skin. Of particular interest in the use of body paint in the material set forth herein is the use by children. However, as used herein, body paint and body painting will be understood to be capable of use in some fashion by adults as well as children.

Products which are utilized as body paint or the like must, of course, be safe for use and be non-toxic in any respect. Also, such products are preferably non-staining to clothing and household fabrics such as tablecloths, drapes or carpets. In further addition, in their preferred formulation, such body paint type products must be washable and removable in simple soap and water washing.

In addition to the requirements that body paint materials be safe, non-toxic and washable, they must of course be sufficiently entertaining and enjoyable to use to promote their success as products. Most typically, such body paint materials are more desirable if they contain bright and exciting colors. In addition, such products are most successful in the marketplace if they are relatively easy to use and apply, particularly by young children. Not surprisingly, the long term popularity of such body paint type play materials has prompted practitioners in the art to provide many different mixtures and formulas for use by young children. For example, U.S. Pat. No. 5,753,244 issued to Reynolds, et al. sets forth a METHOD AND PRODUCT FOR APPLYING SKIN TREATMENTS AND OINTMENTS which utilizes an encapsulated color disappearing or color changing indicator to a topical skin lotion, spray or other similar skin product.

U.S. Pat. No. 5,747,011 issue to Ross, et al. sets forth a SUNSCREEN WITH DISAPPEARING COLOR INDICATOR which employs a water soluble dye or blend of water soluble dyes having color substantially disappearing when the sunscreen emulsion dries after being spread on the skin.

U.S. Pat. No. 5,084,098 issued to Olson sets forth WATER SOLUBLE CRAYON COMPOSITIONS which are comprised of one or more water soluble alkoxylation products and a coloring agent as well as crayons produced therefrom.

U.S. Pat. No. 4,978,390 issued to Snedeker sets forth a WASHABLE SOLID MARKING COMPOSITION which may be formed as a crayon or pencil lead and which is washable from fabrics and other materials. The composition includes a polyethylene glycol resin having a molecular weight of at least 7000 together with a water soluble surfactant.

U.S. Pat. No. 3,993,492 issued to Woolly sets forth a WATER SOLUBLE TRANSFER COATING MATERIAL AND ARTICLES INCORPORATING SAME which is a multi-component mixture including a non-resinated dry pigment having an average particle size between 1 and 5 microns.

U.S. Pat. No. 3,409,574 issued to Gros sets forth MAKING MATERIALS COMPRISING LOW PRESSURE POLYETHYLENE, HIGH PRESSURE POLYETHYLENE AND PLASTICIZER blended in a weight ratio of the former to the latter between 0.25 and 1.5.

U.S. Pat. No. 5,728,762 issued to Reich, et al. sets forth a POLYETHER POLYURETHANE POLYMERS, GELS, SOLUTIONS AND USES THEREOF prepared by reacting a diol component and an organic diisocyanate with critical selection of the amount of water in the reaction mixture and the diol component.

U.S. Pat. No. 5,275,806 issued to Gbogi, et al. sets forth TOPICAL COMPOSITIONS FOR PROTECTION AGAINST ULTRAVIOLET RADIATION which comprise effective amounts of the reaction product of a calcium compound such as calcium hydroxide, calcium oxide, or calcium carbonate with citric acid.

U.S. Pat. No. 5,744,126 issued to Horino, et al. sets forth COSMETICS CONTAINING SILICONE SURFACE-MODIFIED PARTICLES OF TITANIUM OXIDE AND ZINC OXIDE which exhibit good dispersability, high sustained ultraviolet light ray shielding, suppressed photochemical reactivity and catalytic activity of the ultraviolet ray shielding material and high stability.

U.S. Pat. No. 5,735,940 issued to Coller sets forth a MARKING COMPOSITION for producing colors upon contact with a surface, especially one covered with snow or ice. The composition contains a water soluble salt or a mixture of water soluble salts, one or more colorants and water.

U.S. Pat. No. 5,538,548 issued to Yamazaki sets forth a RECORDING INK CONTAINING PIGMENT PARTICLES which is dispersed in an ink solvent. The pigment has a primary particle size not larger than 30nm, a DBP absorption of at least 75ml/100 g, a specific surface area in the range of 100 to 300 square meters per gram and a tinting strength of at least 100.

U.S. Pat. No. 4,472,537 issued to Johnson, et al. sets forth THERMOPLASTIC INKS FOR DECORATING PURPOSES having high viscosity, tacky pastes which exhibit high cohesive strength, high pressure sensitivity at low temperatures, high thermal stability and low affinity for silicone surfaces.

U.S. Pat. No. 4,889,877 issued to Seitz sets forth HIGH SOLIDS CB PRINTING INK prepared by forming microcapsules in situ in a printing ink vehicle. U.S. Pat. Nos. 4,940,739; 4,940,738; and 5,231,117 all of which are continuing or divisional applications of U.S. Pat. No. 4,889,877 and all of which are issued to Seitz show different aspects of similar compounds.

U.S. Pat. No. 4,677,363 issued to Kopmann sets forth a METHOD OF AND APPARATUS FOR MONITORING THE STATE OF CHARGE OF A RECHARGEABLE BATTERY which uses a reference value corresponding to a defined state of charge stored in a memory.

While the foregoing described prior art materials have to some extent improved the art and have in some instances enjoyed commercial success, it has been found generally that the unfortunate circumstance arises in which properties such as safety, non-toxicity, washability and non-staining characteristics often conflict with and require compromise of the desirable properties of body paint materials and the like such as intensity of color, ease of use and/or amusement. Thus, there remains a continuing need in the art for evermore improved and optimized play materials such as body paint or the like.

SUMMARY OF THE INVENTION

Accordingly, it is a general object of the present invention to provide an improved body paint type play material. It is a more particular object of the present invention to provide an improved body paint type play material which forms a solid dry cake of material resistant to transfer by rubbing and requiring the use of a small amount of water and applicator for transfer or application.

In accordance with the present invention, there is provided a body paint formed of two polyethylene glycol waxes, stearic acid, calcium carbonate, talc, titanium dioxide, guar gum, phenonip, and a colorant.

DESCRIPTION OF THE PREFERRED EMBODIMENTS

The present invention body paint material is formed by combining a pair of waxes such as polyethylene glycol-32 and polyethylene glycol-180 together with stearic acid and calcium carbonate. A quantity of talc together with titanium dioxide and guar gum is also added. A preservative and colorant is further added. In the preferred fabrication of the present invention, the ingredients are combined in dry form and mixed as a dry mixture. The mixture takes place at room temperature afterwhich the mixture is subjected to a melting process at an elevated temperature of approximately one hundred fifty degrees centigrade to form a paste consistency. The paste material is then transferred to suitable molds and allowed to cool. When cooling to room temperature, the molded cakes of the material are substantially dry to the touch and resistant to being rubbed off. The resistance to friction rubbing is highly desirable in that transfer of the material in an undesired fashion such as contact with clothing or other fabrics is resisted.

In anticipation of use, the child user employs a conventional applicator having the capability to absorb and retain a quantity of water. The water mixing and applicator is very similar to the process employed with water color paints. Thus, the child user is very familiar with the process used in applying the present invention body paint. The child user may apply the body paint to the desired skin areas and may, for example, mimic face or body painting activities or makeup or cosmetic mimicry as desired. When the desire arises to remove the body paint material, a simple soap and water solution fully removes the body paint from the skin.

The general formula for the present invention body paint material is set forth in Table I.

TABLE I

| Ingredient | Percent by Weight |
| --- | --- |
| Polyethylene Glycol-32 | 15.0 to 22.0 |
| Polyethylene Glycol-180 | 34.0 to 47.0 |
| Stearic Acid | 11.0 to 11.5 |
| Calcium Carbonate | 5.0 to 6.0 |

TABLE I-continued

| Ingredient | Percent by Weight |
| --- | --- |
| Talc | 4.0 to 4.5 |
| Titanium Dioxide | 5.0 to 22.0 |
| Guar Gum | 0.002 to 0.006 |
| Preservative | 0.5 to 0.65 |
| Colorant | 0.5 to 5.5 |

In the above formula, the polyethylene glycol-32 wax may preferably comprise carbowax 1450. Similarly, the polyethylene glycol-180 ingredient set forth above may preferably comprise carbowax 8000. The guar gum ingredient may preferably comprise jaguar 8012. The preservative may preferably include the preservative known phenonip. The selection of preservatives and colorants is largely a matter of choice and the percentages of use thereof is determined in part by the materials selected.

The present invention material formula may be adjusted to accommodate a variety of colors.

Thus, specific formulas for a number of colors are set forth in Tables II through IX as is Table I above. Tables II through are set forth below. By way of overview, it will be apparent that the formulas set forth in Tables II through IV include the same basic ingredients in closely similar percentages. These basic ingredients include carbowax 1450, carbowax 8000, stearic acid, calcium carbonate, talc, titanium dioxide, jaguar 8012 and phenonip. Carbowax 1450 and Carbowax 8000 are both polyethylene glycol waxes. Stearic acid, calcium carbonate, talc and titanium dioxide are of course generic compound names. Jaguar 8012 is a commercial name of a guar gum and phenonip is a well known preservative. These basic elements are found in substantially the same percentages in each of Tables II through IX set forth below with the exception of Table IX which corresponds to a black material formulation. In the mixture of basic ingredients in the black material of Table IX, a substantial reduction in the amount of titanium dioxide is coupled with a substantial increase in the amount of carbowax 8000. This is primarily carried forward to enable the black iron oxide coloring material to be unhampered by a large quantity of titanium dioxide.

More specifically, Table II sets forth the formulation for the present invention body paint material in which a peach color is desired.

TABLE II

| Ingredient | Percent by Weight |
| --- | --- |
| Carbowax 1450 | 15.8 |
| Carbowax 8000 | 34.7 |
| Stearic Acid | 11.0 |
| Calcium Carbonate | 5.3 |
| Talc | 4.0 |
| Titanium Dioxide | 20.6 |
| Jaguar 8012 | 0.005 |
| Phenonip | 0.58 |
| FD&C Yellow No. 5 Al Lake | 4.8 |
| FD&C Red No. 40 Al Lake | 3.2 |

Table III sets forth the formula for the present invention body paint material in which a green color is desired.

TABLE III

| Ingredient | Percent by Weight |
| --- | --- |
| Carbowax 1450 | 16.5 |
| Carbowax 8000 | 36.3 |
| Stearic Acid | 11.5 |
| Calcium Carbonate | 5.5 |
| Talc | 4.3 |
| Titanium Dioxide | 21.4 |
| Jaguar 8012 | 0.006 |
| Phenonip | 0.6 |
| FD&C Yellow No. 5 Al Lake | 3.4 |
| FD&C Blue No. 1 Al Lake | 0.6 |

Table IV sets forth the formula for the present invention body paint material in which a pink color is desired.

TABLE IV

| Ingredient | Percent by Weight |
| --- | --- |
| Carbowax 1450 | 16.5 |
| Carbowax 8000 | 36.1 |
| Stearic Acid | 11.5 |
| Calcium Carbonate | 5.5 |
| Talc | 4.3 |
| Titanium Dioxide | 21.5 |
| Jaguar 8012 | 0.006 |
| Phenonip | 0.6 |
| FD&C Red No. 40 Al Lake | 4.0 |

Table V sets forth the formula for the present invention body paint material in which a purple color is desired.

TABLE V

| Ingredient | Percent by Weight |
| --- | --- |
| Carbowax 1450 | 16.5 |
| Carbowax 8000 | 36.1 |
| Stearic Acid | 11.5 |
| Calcium Carbonate | 5.5 |
| Talc | 4.3 |
| Titanium Dioxide | 21.5 |
| Jaguar 8012 | 0.006 |
| Phenonip | 0.6 |
| FD&C Blue No. 1 Al Lake | 0.63 |
| Manganese Violet | 3.4 |

Table VI sets forth the formula for the present invention body paint material in which a yellow color is desired.

TABLE VI

| Ingredient | Percent by Weight |
| --- | --- |
| Carbowax 1450 | 16.5 |
| Carbowax 8000 | 36.1 |
| Stearic Acid | 11.5 |
| Calcium Carbonate | 5.5 |
| Talc | 4.3 |
| Titanium Dioxide | 21.5 |
| Jaguar 8012 | 0.006 |
| Phenonip | 0.6 |
| FD&C Yellow No. 5 Al Lake | 4.0 |

Table VII sets forth the formula for the present invention body paint material in which an aqua color is desired.

TABLE VII

| Ingredient | Percent by Weight |
| --- | --- |
| Carbowax 1450 | 16.5 |
| Carbowax 8000 | 36.1 |
| Stearic Acid | 11.5 |
| Calcium Carbonate | 5.5 |
| Talc | 4.3 |
| Titanium Dioxide | 21.5 |
| Jaguar 8012 | 0.006 |
| Phenonip | 0.6 |
| FD&C Green No. 5 Al Lake | 4.0 |

Table VIII sets forth the formula for the present invention body paint material in which a white color is desired.

TABLE VIII

| Ingredient | Percent by Weight |
| --- | --- |
| Carbowax 1450 | 18.5 |
| Carbowax 8000 | 38.1 |
| Stearic Acid | 11.5 |
| Calcium Carbonate | 5.5 |
| Talc | 4.3 |
| Titanium Dioxide | 21.5 |
| Jaguar 8012 | 0.006 |
| Phenonip | 0.6 |

Table IX sets forth the formula for the present invention body paint material in which a black color is desired.

TABLE IX

| Ingredient | Percent by Weight |
| --- | --- |
| Carbowax 1450 | 21.9 |
| Carbowax 8000 | 48.7 |
| Stearic Acid | 11.9 |
| Calcium Carbonate | 5.7 |
| Talc | 4.4 |
| Titanium Dioxide | 1.6 |
| Jaguar 8012 | 0.006 |
| Phenonip | 0.6 |
| Black Iron Oxide | 5.2 |

Thus, in the above formulations and the general formula set forth above in Table I, the materials are mixed initially as dry granular materials are room temperature and thereafter subjected to a high temperature melt at approximately one hundred fifty degrees centigrade. The high temperature melt is, as described above, utilized to form a paste allowing the material to then be transferred to a suitably shaped forming mold for cooling. Once cooled, the body paint material takes the form of a dry cake having a substantial binder and being substantially resistant to rubbing or touching against material such as cloth fabric or the like. This higher binding strength reduces the likelihood of inadvertent or undesired staining of clothing and other household fabrics.

When in use, the body paint material is activated by utilizing a water moistened applicator which is rubbed upon the surface of the cake material until the desired body paint consistency is obtained. Thereafter, the applicator bearing the water solution of the body paint material may be used to color skin areas as desired. The use of the body paint material as a dry cake is further protection against accidental tipping or spilling or other mishaps likely to occur as young children use coloring materials.

The present invention body paint material is readily removed from skin and other surfaces by a simple soap and water washing solution.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. A washable non-toxic body paint which forms a water soluble dry paste, said body paint comprising the following ingredients in percentages by weight:

| | |
|---|---|
| Polyethylene Glycol-32 | 15.0 to 22.0 |
| Polyethylene Glycol-180 | 34.0 to 47.0 |
| Stearic Acid | 11.0 to 11.5 |
| Calcium Carbonate | 5.0 to 6.0 |
| Talc | 4.0 to 4.5 |
| Titanium Dioxide | 5.0 to 22.0 |
| Guar Gum | 0.002 to 0.006 |
| Preservative | 0.5 to 0.65 |
| Colorant | 0.5 to 5.5. |

* * * * *